United States Patent [19]

Goldberg et al.

[11] Patent Number: 4,932,938
[45] Date of Patent: Jun. 12, 1990

[54] URETHRAL INDWELLING CATHETER WITH INCONTINENCE CONTROL

[75] Inventors: Jay R. Goldberg, Libertyville, Ill.; Frank P. Gregory; Donald L. Anderson, Jr., both of Racine, Wis.

[73] Assignee: Medical Engineering Corporation, Racine, Wis.

[21] Appl. No.: 348,524

[22] Filed: May 5, 1989

[51] Int. Cl.$^5$ .............................................. A61M 25/00
[52] U.S. Cl. ...................... 604/96; 604/104; 604/247; 251/342; 606/30
[58] Field of Search ............. 604/54, 96, 247, 246, 604/256, 249, 104, 105; 251/342, 350; 606/30

[56] References Cited

U.S. PATENT DOCUMENTS

| | | | |
|---|---|---|---|
| 2,518,165 | 8/1950 | Millard | 251/342 |
| 2,706,101 | 4/1955 | Cantor | 251/342 |
| 3,672,372 | 6/1972 | Heimuch | 604/247 |
| 3,967,645 | 7/1976 | Gregory | 604/247 |
| 4,346,714 | 8/1982 | Child | 604/54 |
| 4,535,818 | 8/1985 | Duncan et al. | 604/247 |
| 4,553,959 | 11/1985 | Aickey et al. | 604/247 |

*Primary Examiner*—Stephen C. Pellegrino
*Attorney, Agent, or Firm*—Stuart E. Krieger

[57] ABSTRACT

The catheter includes a user-controlled incontinence portion that is combinable with a fluid drainage member to permit continuous bladder drainage into a fluid collection member. The fluid drainage member can be detached from the incontinence portion of the catheter while the catheter is installed in the urethra and bladder to convert from a continuous drainage system to a user-controlled system. In some embodiments of the invention the fluid drainage member includes inflation lumen for inflating a bladder balloon and urethral cuff of the incontinence portion. In other embodiments of the invention the bladder engaging portion and the urethral cuff are noninflatable and can be either compressed or distended to facilitate insertion in the urethra and bladder. A palpatable valve means is palpatable through the penis to an open condition to permit user-controlled bladder drainage. The valve means in several embodiments of the invention is maintained in a continuously open condition when the fluid drainage portion is joined to the incontinence portion. In another embodiment of the invention the valve means can still be palpated to an open or closed condition when the fluid drainage system is joined to the incontinence portion.

22 Claims, 8 Drawing Sheets

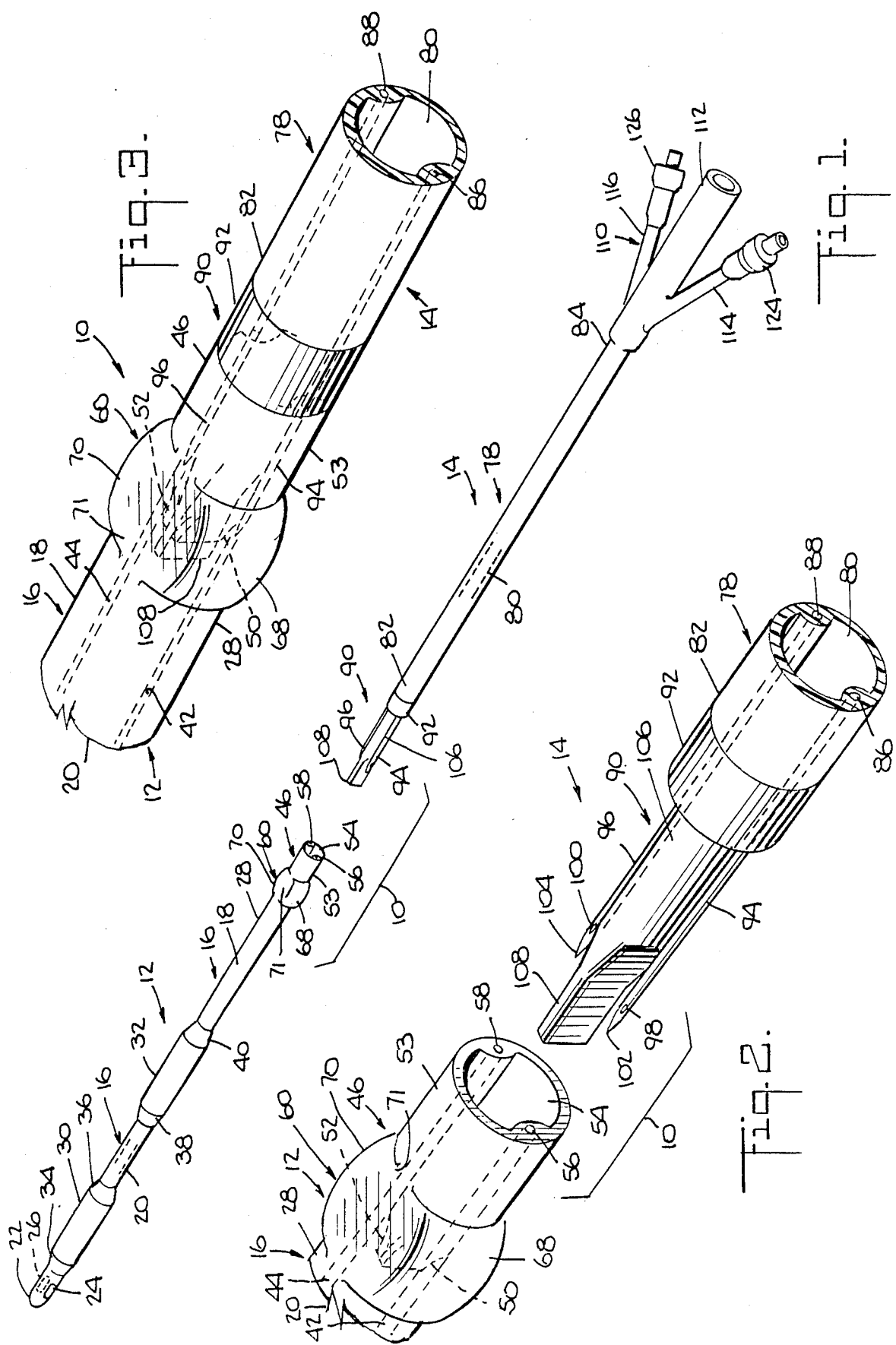

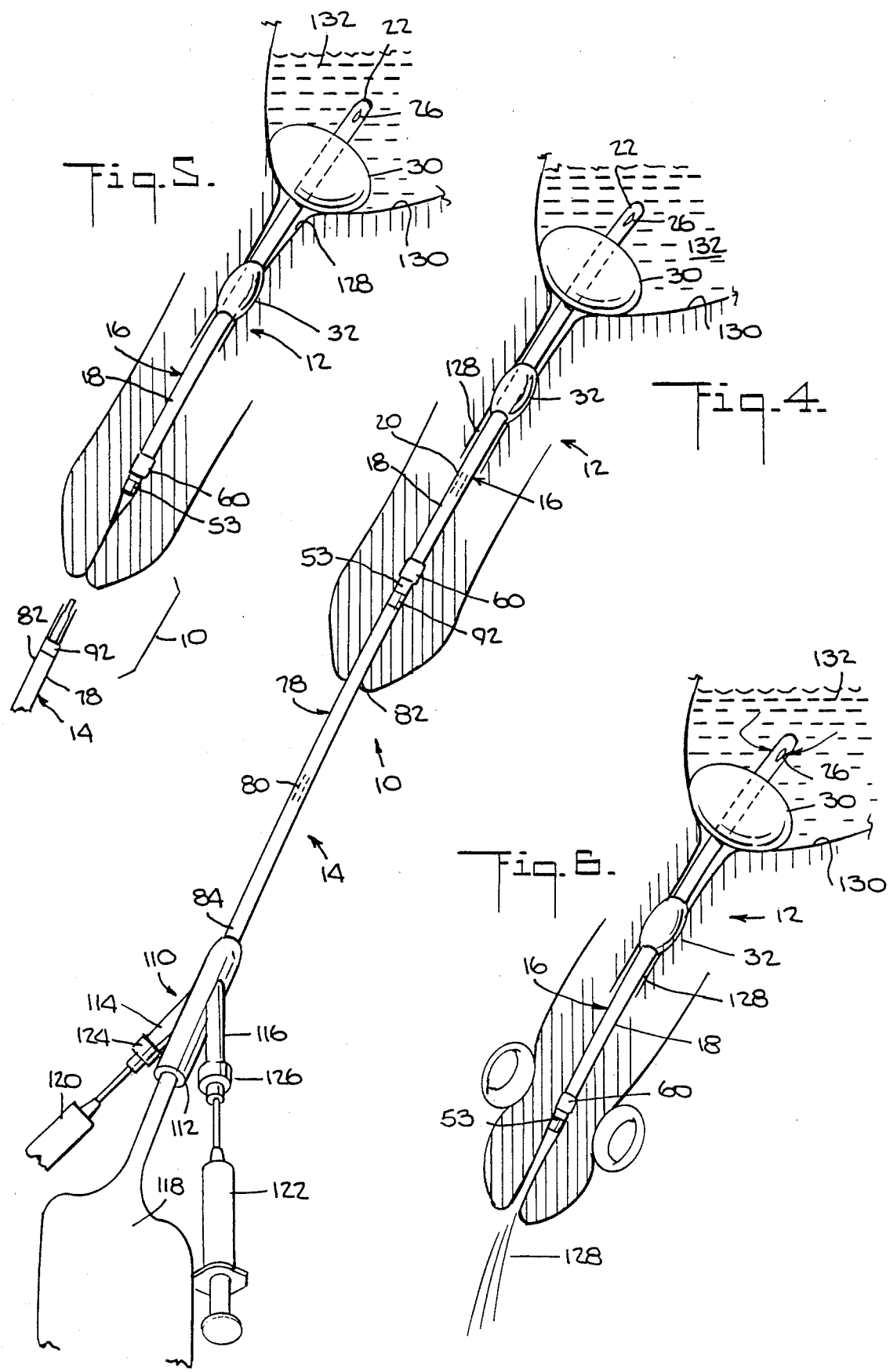

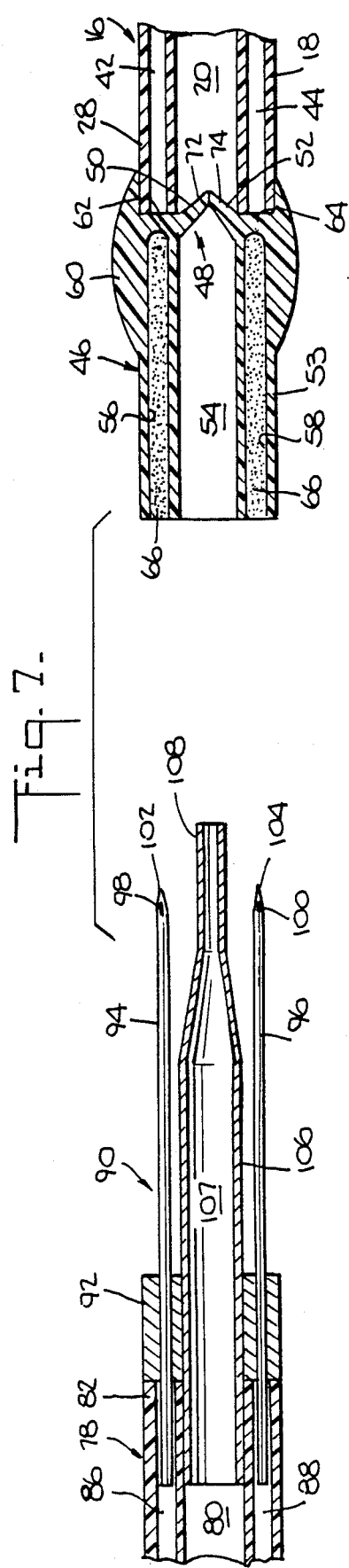
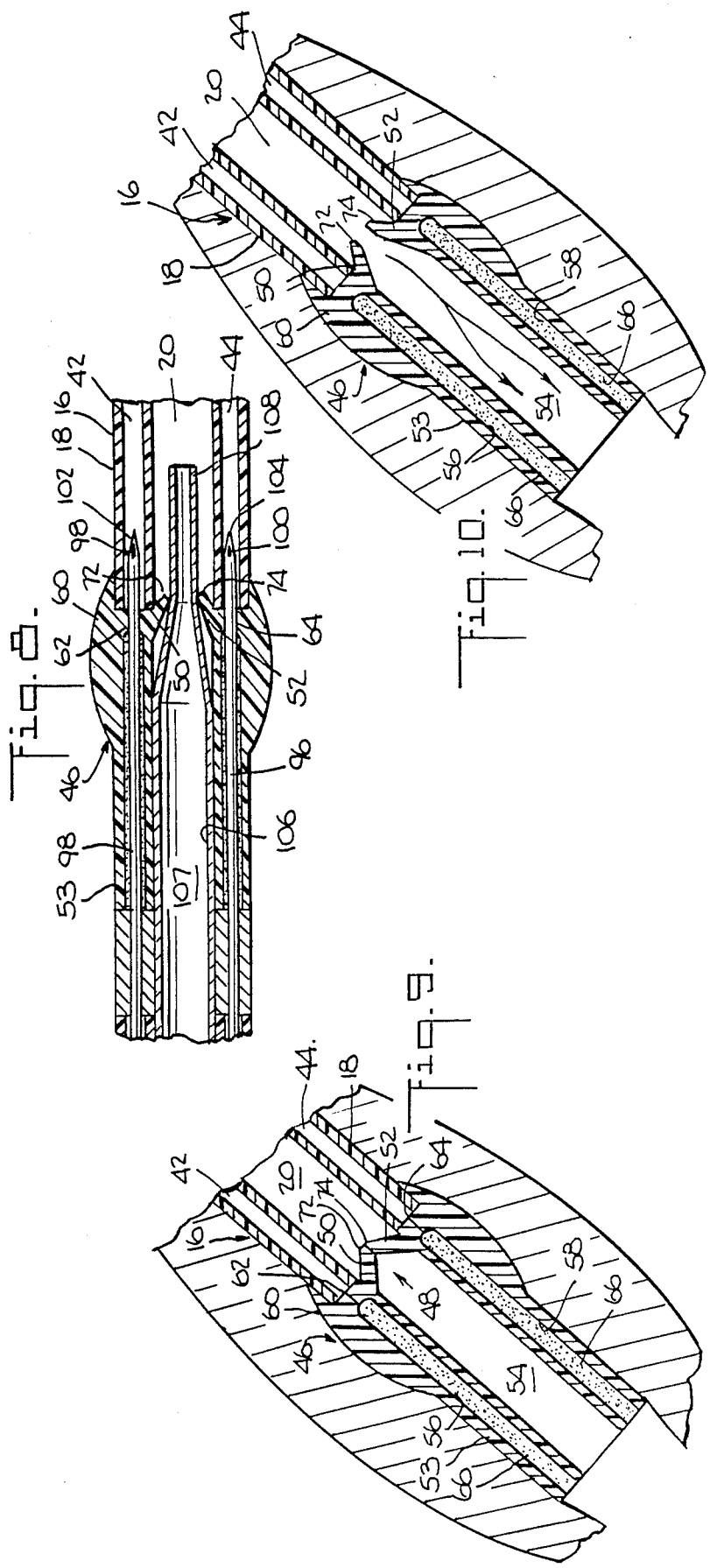

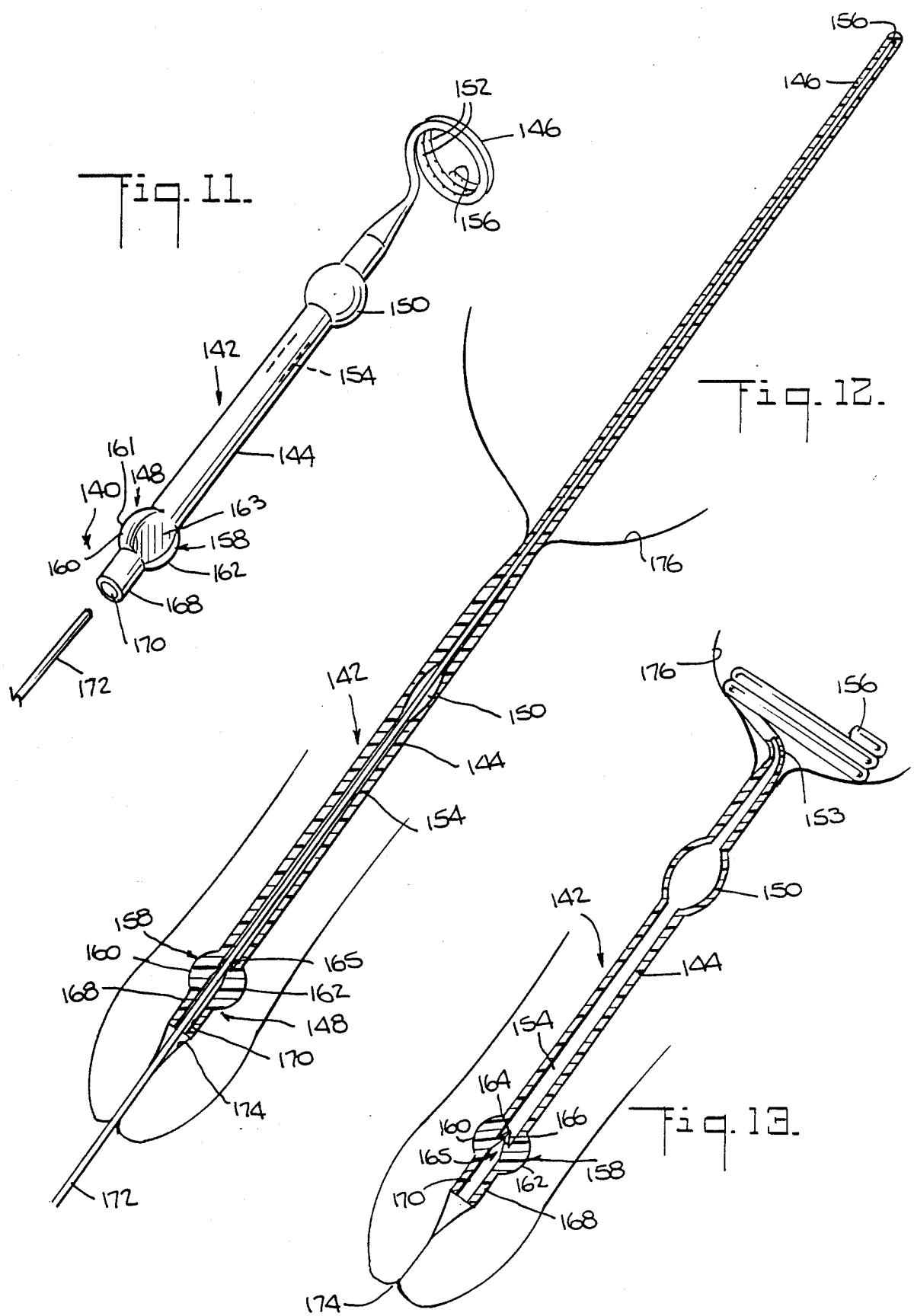

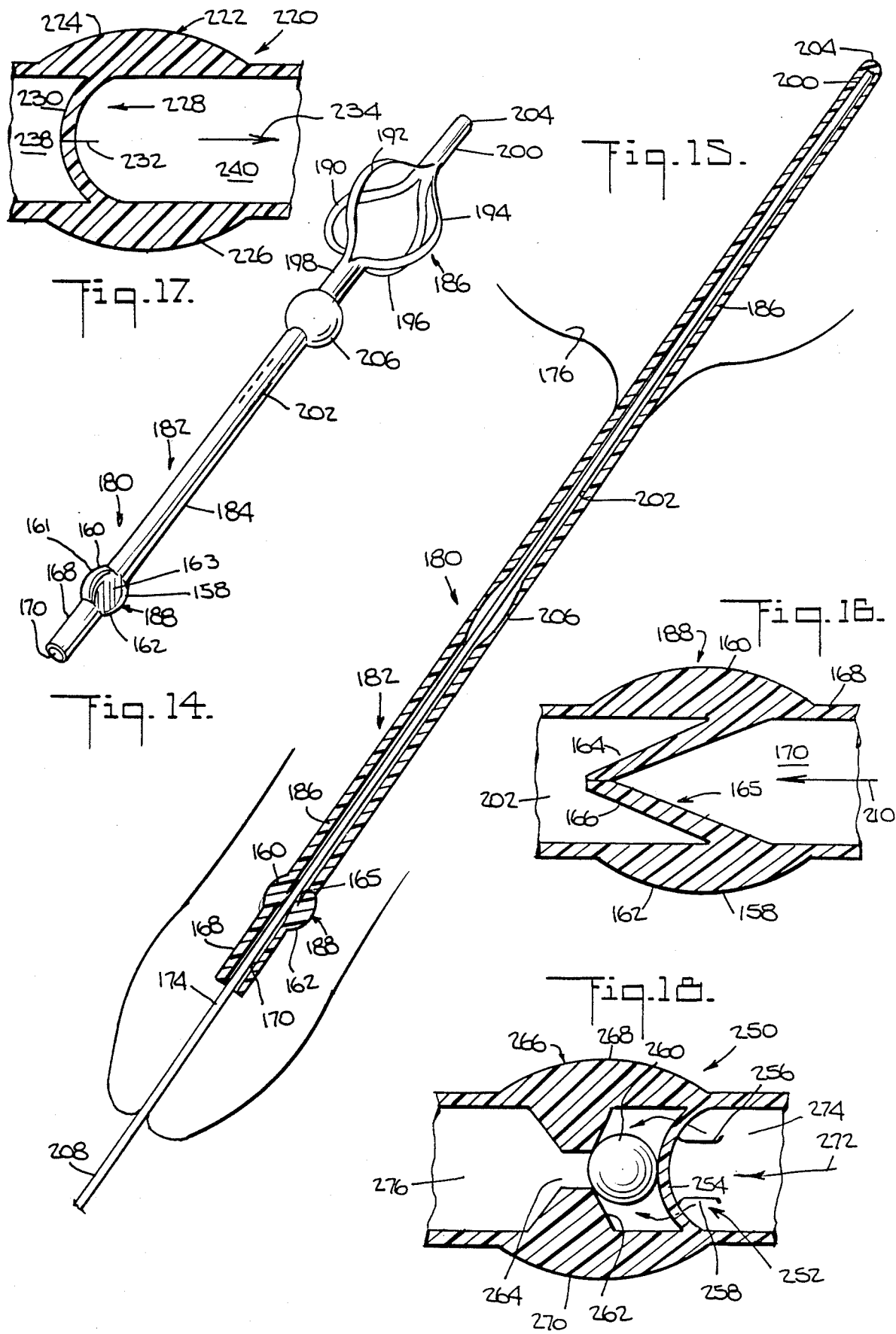

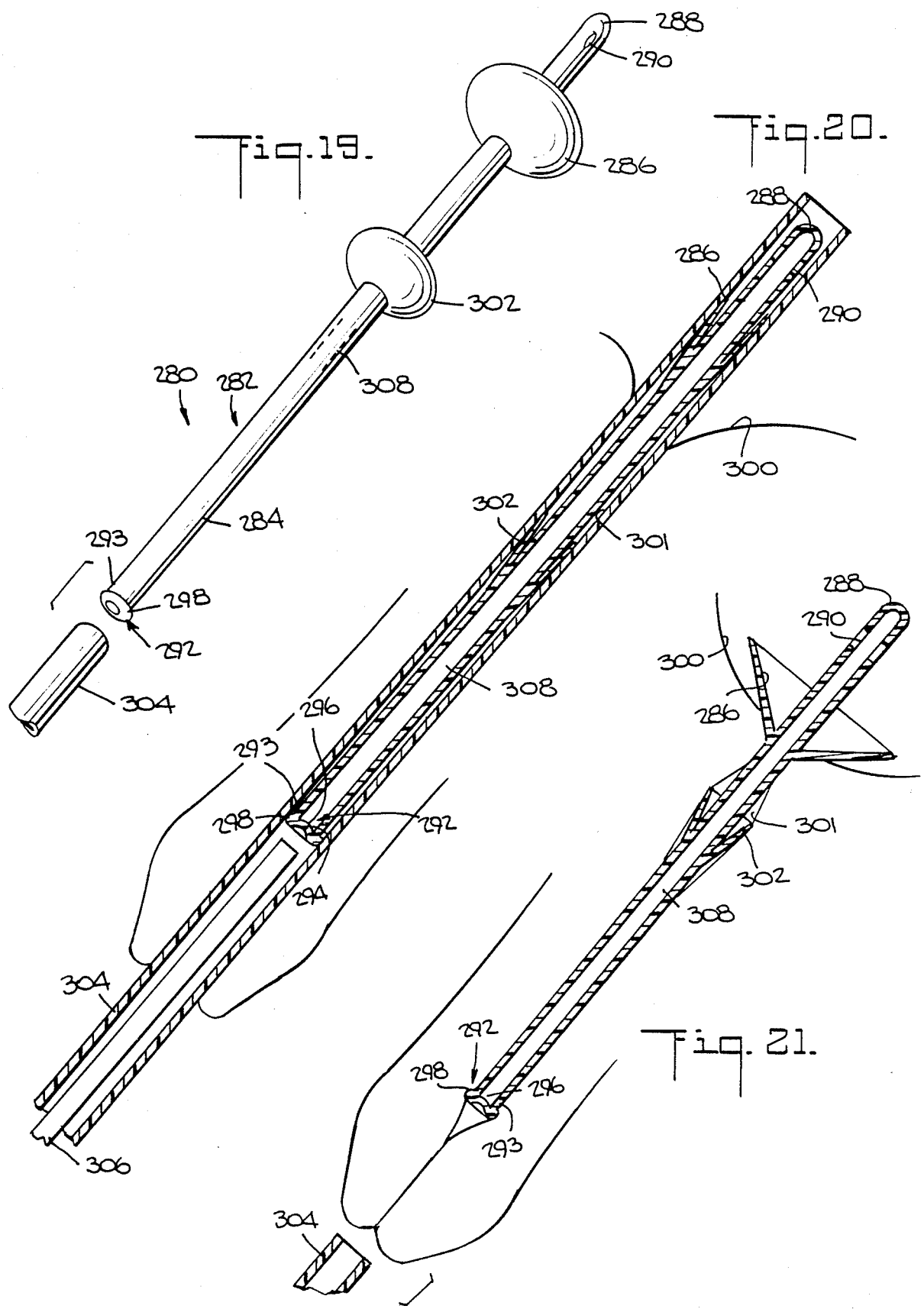

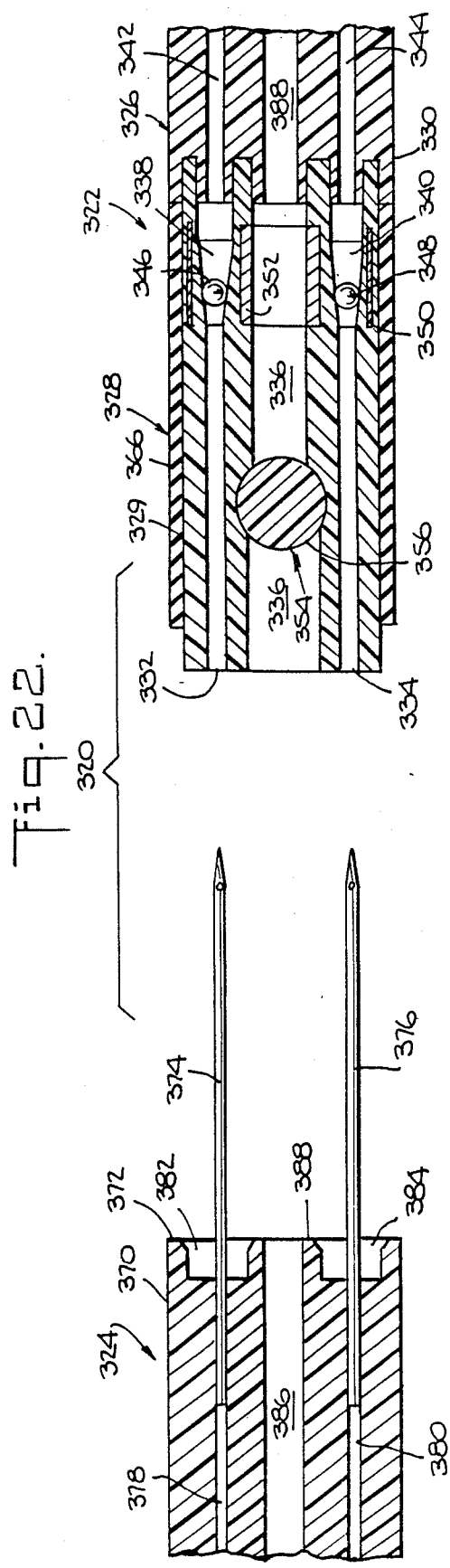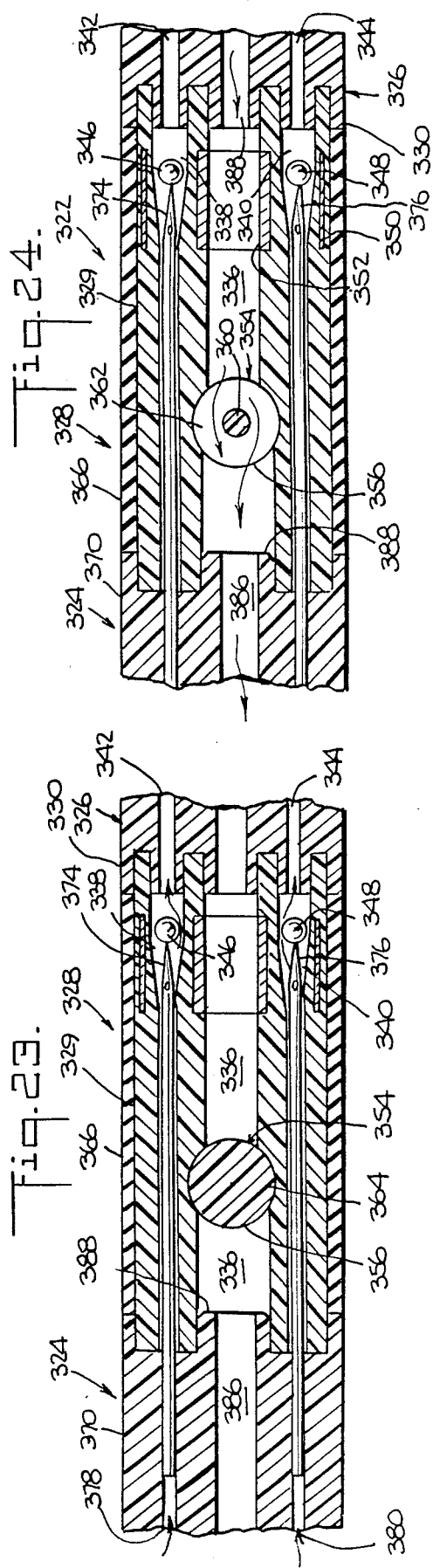

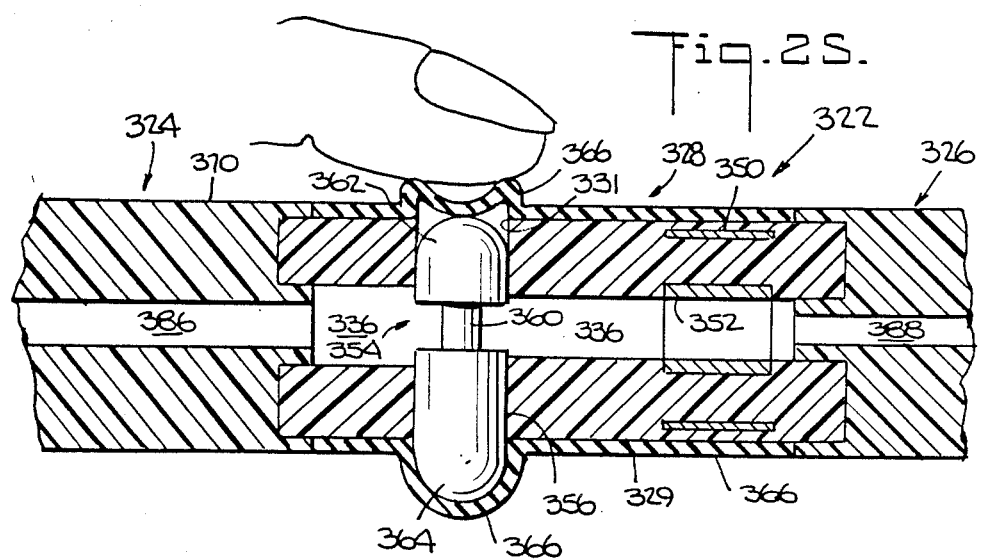
Fig. 25.
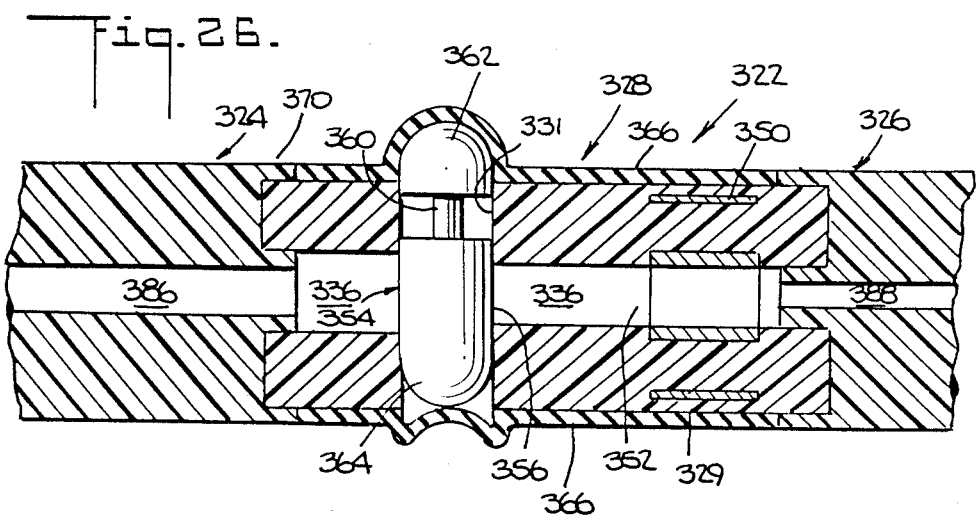
Fig. 26.
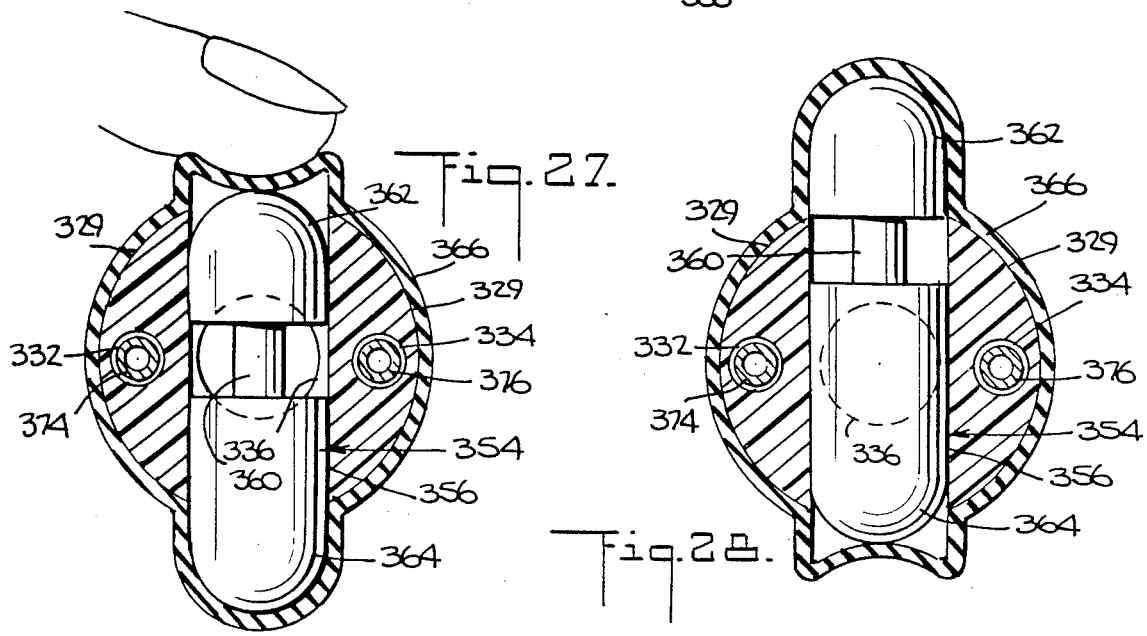
Fig. 27.
Fig. 28.

1

URETHRAL INDWELLING CATHETER WITH INCONTINENCE CONTROL

BACKGROUND OF THE INVENTION

This invention relates to catheters and more particularly to an indwelling catheter which can be used for continuous bladder drainage or adapted to function as a user controlled incontinence device.

Indwelling urethral catheters have long been used to facilitate bladder drainage in individuals who are unable to initiate or control such drainage due to organic disability, immobility, or other physical impairment.

In some instances a patient will be rendered immobile on a temporary basis due to medical complications or other impediment, and the nature of the disability will require use of a catheter with a collection arrangement that permits continuous bladder drainage.

Continuous drainage catheters, wherein fluid draining from the bladder flows into a collection bag that can be emptied as needed, are shown, for example, in U.S. Pat. Nos. 3,981,299; 3,924,634; 3,811,450; 3,805,794; and 3,769,981.

Occasionally it may be advisable for a patient to change from a continuous drainage catheter to one which permits user controlled bladder drainage. Such a change often requires replacement of the continuous drainage catheter with an incontinence control device that enables the user to control bladder discharges through user controlled valves, such as shown in U.S. Pat. Nos. 3,331,371; 3,768,102; 4,026,298 and 4,350,161.

The installation and/or removal of a continuous drainage catheter will sometimes cause irritation. When the removal of a continuous drainage catheter is followed by the installation of a replacement catheter that is user controlled, further discomfort may be experienced.

It is thus desirable to provide an indwelling urethral catheter that can be used for continuous drainage of fluid from a bladder and, without replacing the urethral installation of the catheter, can be adapted to function as an incontinence control device that permits user controlled bladder drainage.

OBJECTS AND SUMMARY OF THE INVENTION

Among the several objects of the invention may be noted the provision of a novel indwelling urethral catheter with incontinence control, a novel indwelling urethral catheter with incontinence control having a manually manipulable control valve for controlling bladder drainage, a novel urethral indwelling catheter with incontinence control capability that permits continuous drainage of fluid from the bladder and can be adapted to permit user controlled bladder drainage through a manually manipulable valve, a novel urethral indwelling catheter with an incontinence control valve that can be entirely recessed within the penis in substantially undetectable fashion, a novel indwelling urethral catheter with an incontinence control valve that can be easily palpated through the penis, a novel urethral indwelling catheter for continuous drainage of fluid through a normally closed incontinence control valve by use of a collection arrangement that maintains the incontinence control valve in a continuously open condition, and a novel method of draining fluid from a bladder.

Other objects and features of the invention will be in part apparent and in part pointed out hereinafter.

The indwelling urethral catheter with incontinence control, in accordance with one embodiment of the invention, includes a flexible elongated tubular member having a fluid drainage passage. The tubular member has bladder engaging means provided at one end portion to engage the bladder wall and restrain movement of the tubular member away from the bladder. The tubular member also includes an opening in proximity of the bladder engaging means that communicates with the drainage passage to drain fluid from the bladder into the tubular member.

A urethra engaging member is provided on the wall of the tubular member to engage a predetermined portion of the urethra. The bladder engaging means and the urethra engaging means thus cooperate to prevent movement of the tubular member from a predetermined position in the urethra and bladder.

Valve means for controlling incontinence are provided at an opposite end portion of the tubular member to control movement of fluid through the drainage passage. The valve means includes a valve member in a normally closed position. The valve means is manually manipulable by palpation to an open condition.

As used herein, the term palpate is intended to refer to the touching, pressing or squeezing of a valve member to deflect the valve member. The term deflect contemplates compression or slidable movement of the valve member.

In several embodiments of the invention, the valve means include a deflectable valve member that, during palpation, compresses to an open condition. In another embodiment of the invention, the valve means includes a deflectable valve member that, during palpation, slidably moves to an open position.

In order to permit continuous bladder drainage, a drainage fluid collection arrangement is joined to the tubular member at the valve means. The drainage fluid collection arrangement includes a duct member engagable with the valve member to cause the valve member to assume an open position.

The duct member thus maintains the normally closed valve member in a continuous open position during such engagement. During bladder drainage, fluid flows through the tubular member past the open valve member through the duct member and into a drainage fluid collection bag provided at the end of the duct member.

In a further embodiment of the invention, the bladder engaging means is inflatable as is the urethra engaging means. The drainage fluid collection arrangement and tubular member also include an inflation means for inflating the bladder engaging section and the urethra engaging section.

When it is desired to convert the catheter from a continuous drainage function to an incontinence control device for user controlled urination, the drainage fluid collection arrangement is detached without removing the tubular member from its installed position in the urethra.

Detachment of the drainage fluid collection arrangement enables the valve member to assume its normally closed position. Separate inflation sealing means are provided in the tubular member to prevent escape of inflation fluid when the drainage fluid collection arrangement is detached. The tubular member thus remains installed in the urethra when the catheter is adapted to function as an incontinence control device that permits user controlled bladder drainage.

In using the catheter as an incontinence control device, the valve means is manually manipulable by palpation through the penile meatus. Lobed portions on the tubular member at the valve means facilitate palpation of the valve to cause deflection of a valve member that places the valve means in an open condition. In several embodiments when palpation ceases, the valve means returns to a normally closed condition to stop bladder drainage. In another embodiment when palpation is removed, the valve means remains in the palpated position.

In a further embodiment of the invention, the bladder engaging means comprises a spiral formation at the bladder engaging end of the tubular member. The urethra engaging means includes a preformed bulge on the tubular member. Both the spiral formation and the urethral bulge can be straightened and distended by a stylet to facilitate insertion in the urethra and bladder.

In another embodiment of the invention, the bladder engaging means includes a Malecot portion formed at the bladder engaging end of the tubular member. The Malecot formation is also straightened and distended by a stylet to facilitate insertion in the urethra and bladder.

A further embodiment of the invention includes funnel-shaped bladder engaging and urethra engaging portions flexibly protruding from the tubular member at the bladder engaging section and the urethra engaging section. Urethral and bladder insertion is accomplished by use of a sleeve to surround the tubular member to compress the funnel-shaped bladder and urethra engaging sections within the confines of the sleeve, thereby facilitating insertion of the tubular member in the urethra and bladder.

The invention accordingly comprises the constructions and method hereinafter described, the scope of the invention being indicated in the claims.

DESCRIPTION OF THE DRAWINGS

In the accompanying drawings,

FIG. 1 is a dissembled perspective view of the indwelling urethral catheter with incontinence control;

FIG. 2 is an enlarged fragmentary perspective view thereof;

FIG. 3 is a view similar to FIG. 2 in assembled condition;

FIG. 4 is an elevational perspective view thereof in operational position for continuous drainage of fluid from the bladder into a collection bag;

FIG. 5 is an elevational view thereof adapted for incontinence control with the collection and inflation arrangement removed;

FIG. 6 is an elevational view thereof showing the valve means being palpated to permit bladder discharge;

FIG. 7 is an enlarged dissembled fragmentary sectional view thereof;

FIG. 8 is an enlarged fragmentary sectional view thereof in assembled condition;

FIG. 9 is an enlarged fragmentary view thereof in operational position in the urethra and bladder, adapted for incontinence control with the collection and inflation arrangement removed and the valve means in a normally closed position;

FIG. 10 is a view similar to FIG. 9 showing the valve means palpated to an open position;

FIG. 11 is a perspective view of another embodiment thereof;

FIG. 12 is a sectional view thereof during installation in the urethra and bladder;

FIG. 13 is a sectional view thereof after installation in the urethra and bladder;

FIG. 14 is a perspective view of a further embodiment thereof;

FIG. 15 is a sectional view thereof during installation in the urethra and bladder;

FIG. 16 is an enlarged fragmentary sectional view of the valve means thereof;

FIGS. 17-18 are enlarged fragmentary sectional views of other embodiments of valve means thereof;

FIG. 19 is a perspective view of a further embodiment thereof;

FIG. 20 is a sectional view thereof during installation in the urethra and bladder;

FIG. 21 is a sectional view thereof after installation in the urethra and bladder;

FIG. 22 is an enlarged dissembled fragmentary sectional view of another embodiment thereof;

FIG. 23 is an enlarged fragmentary sectional view thereof in assembled condition with the control valve means in a closed position;

FIG. 24 is a view similar to FIG. 23 with the control valve means in an open position;

FIG. 25 is an enlarged fragmentary sectional view thereof showing the control valve means palpated into an open position;

FIG. 26 is a view similar to FIG. 25 with the control valve means in a normally closed position;

FIG. 27 is an enlarged end sectional view thereof corresponding to FIG. 25; and

FIG. 28 is an enlarged end sectional view thereof corresponding to FIG. 26.

Corresponding reference characters indicate corresponding parts throughout the several views of the drawings.

DETAILED DESCRIPTION OF THE INVENTION

A catheter assembly incorporating one embodiment of the invention is generally indicated by the reference number 10 in FIG. 1.

The catheter assembly 10 includes an incontinence portion 12 and a drainage/inflation member 14 adapted to be detachably joined to the incontinence portion 12.

The incontinence portion 12 comprises an elongated tubular member 16 which can be formed of silicone. The tubular member 16 has an outside tubular surface 18 and an interior fluid drainage passage 20.

One end portion 22 of the tubular member 16 is provided with oppositely disposed openings 24 and 26 that communicate with the drainage passage 20. The drainage passage 20 thus extends from the end portion 22 of the tubular member 16 to an opposite end portion 28 of the tubular member 16.

An inflatable bladder balloon 30, preferably formed of silicone is joined to the periphery of the tubular member 16 at a predetermined distance from the end portion 22. An inflatable urethral cuff 32 also formed of silicone is joined to the periphery of the tubular member 16 at a predetermined distance from the bladder balloon 30. The bladder balloon 30 and the urethral cuff 32 are initially deflated as shown in FIG. 1.

Opposite end portions 34 and 36 of the bladder balloon 30 are secured to the outer surface 18 of the tubular member 16 in leak-tight arrangement using a suitable known silicone adhesive. In similar fashion, opposite end portions 38 and 40 of the urethral cuff 32 are secured to the tubular surface 18 of the tubular member 16 in leaktight fashion.

As most clearly shown in FIG. 8, a pair of inflation lumen 42 and 44 are formed on the interior of the tubular member 16. The inflation lumen 42, for example, communicates with the bladder balloon 30, and the inflation lumen 44 communicates with the urethral cuff 32.

Referring to FIGS. 1-3 and 7, a generally tubular valve junction 46 joins the end portion 28 of the tubular member 16. The valve junction 46 includes a valve means 48 comprising duckbill valve portions 50 and 52 provided across the fluid drainage passage 20 of the tubular member 16. The duckbill portions 50 and 52, which can be formed of silicone, are in a normally closed position, thus closing off the fluid drainage passage 20.

The junction member 46 also includes a tubular section 53 having a fluid passage 54 corresponding to the fluid drainage passage 20 and lumen portions 56 and 58 corresponding to the inflation lumen 42 and 44. A cuff-like portion 60 which can be formed of silicone is provided around the periphery of the junction member 46 surrounding the duckbill valve portions 50 and 52.

A pair of palpation lobes 68 and 70 are formed in opposite disposition on the cuff portion 60 in alignment with the respective lumen 56 and 58. Oppositely disposed flat palpation portions 69 and 71 are formed on the cuff portion 60 at the cheek side of the duckbill valve portions 50 and 52, between the palpation lobes 68 and 70.

An inflation seal portion 62 (FIG. 7) is formed at a terminus of the lumen 56 and a corresponding inflation seal portion 64 is formed at a terminus of the lumen 58. The inflation seal portions 62 and 64 normally prevent communication from the lumen 56 to the lumen 42 and from the lumen 58 to the lumen 44. Self sealing gel 66 which can be formed of silicone gel is disposed in the lumen portions 56 and 58.

The drainage/inflation member 14 comprises a drainage duct member 78 having an interior duct passage 80 that extends from an end portion 82 to an opposite end portion 84. The drainage duct member can be formed of silicone, polyvinyl chloride, or any other suitable known biocompatible thermoplastic.

A pair of inflation lumen 86 and 88 (FIG. 2) corresponding to the inflation lumen 56 and 58 are formed on the inner surface of the duct passage 80.

An engagement assembly 90 formed of a suitable metal such as stainless steel, includes a cap portion 92 adapted to form a leak-tight seal around the end portion 82 of the drainage duct member 78. A pair of inflation needles 94 and 96, having respective inflation openings 98 and 100, extend longitudinally from the cap portion 92. The inflation needles 94 and 96 align with and form a continuation of the inflation lumen 86 and 88. Piercing points 102 and 104 are formed at the respective free ends of the inflation needles 94 and 96.

A duct extension piece 106 which can be formed of stainless steel, projects from the cap portion 92 intermediate the inflation needles 94 and 96. The duct extension 106 defines a duct extension passage 107 that is a continuation of the duct passage 80 and has a reduced open free end portion 108 having a generally rectangular cross section.

A branch member 110 (FIGS. 1 and 4) joins the end portion 84 of the drainage duct member 78 and includes a drainage extension 112 that communicates with the duct passage 80. The branch member 110 also includes syringe receivers 114 and 116 that respectively communicate with the inflation lumen 86 and 88.

In using the catheter assembly 10, the drainage/inflation member 14 is joined to the incontinence portion 12 by aligning the inflation needles 94 and 96 with the lumen portions 56 and 58 of the junction member 46 as shown in FIG. 2. The free end portion 108 of the duct extension 106 will thus be received in the fluid passage 54 of the tubular section 53 as the inflation needles 94 and 96 are received in the lumen portions 56 and 58 for engagement in the manner shown in FIG. 3. The periphery of the tubular section 53 is substantially identical to the periphery of the cap portion 92 to provide a smooth continuous surface where the junction member 46 and the engagement assembly 90 merge.

The inflation needles 94 and 96, as they pass into the lumen portions 56 and 58, pierce the respective inflation seal portions 62 and 64 for entry into the inflation lumens 42 and 44 of the tubular member 16 as shown in FIG. 8. The self sealing gel 66 in the lumens 56 and 58 ensures leak tight engagement of the inflation needles 94 and 96 with the seal portions 62 and 64.

The free end portion 108 of the duct extension 106 passes between the duckbill valve portions 50 and 52 separating the confronting lips 72 and 74 to maintain the duckbill valve portions 50 and 52 in an open position. A direct line of communication between the fluid drainage passage 20, the duct extension passage 107, the duct passage 80 and the drainage extension 112 is thus established. A collection bag 118 (FIG. 4) is connected to the drainage extension 112 and respective syringes 120 and 122 are positioned in the syringe receivers 114 and 116 with appropriate predetermined amounts of a suitable known inflation fluid.

After the incontinence portion 12 and the drainage/inflation member 14 are joined together, a suitable known lubricant (not shown) is applied to the tubular surface 18 of the tubular member 16. The tubular member 16 is inserted into the urethra 128 to position the uninflated bladder balloon 30 in the bladder 130. The tubular member 16 is sized such that the cuff portion 60 of the junction member 46 substantially aligns with the penile meatus. Tubular members 16 of various different lengths can be inventoried to ensure such alignment with the penile meatus.

With the uninflated bladder balloon 30 thus positioned in the bladder 130, the syringes 120 and 122 can be operated to force fluid through the respective lumen passages 86-56-42 and 88-58-44 to inflate the bladder balloon 30 and the urethral cuff 32 in the manner shown in FIG. 4.

When inflation is completed, the syringes 120 and 122 are removed and self-sealing valves 124 and 126 provided on the syringe receivers 114 and 116 ensure that the inflation volume of the bladder balloon 30 and the urethral cuff 32 is maintained.

Bladder fluid 132 (FIG. 4) is thus enabled to pass into the openings 24 and 26 for passage through the fluid drainage passage 20, into the duct extension passage 107 and through the duct passage 80 into the collection bag 118. There is no communication between the fluid passages 20, 107, 80 and the inflation lumens 42, 44, 56, 58 and 86, 88.

Under this arrangement, bladder fluid 132 continuously drains from the bladder 130 past the duckbill valve portions 50 and 52 into the collection bag 118. The filled collection bag 118 can be emptied or replaced as a matter of choice.

When it is feasible for a patient to control his own bladder drainage, the drainage/inflation member 14 is detached from the tubular section 53 in the manner shown in FIG. 5. Thus the patient can manually pinch or compress the penis just proximal to the junction of the incontinence portion 12 and the drainage/inflation member 14. Pinching prevents antegrade migration (dislocation) of the catheter.

As the drainage/inflation member 14 is separated from the incontinence portion 12, the inflation needles 94 and 96 are withdrawn from the lumen 56 and 58. The self sealing gel 66 thus seals the puncture openings in the inflation seal portions 62 and 64 caused by the needles 94 and 96. Inflation volume of the bladder balloon 30 and urethral cuff 32 is thus maintained. Withdrawal of the free end portion 108 of the duct extension 106 from the junction member 46 enables the duckbill valve portions 50 and 52 to resume their normally closed positions thereby shutting off the fluid drainage passage 20. The bladder fluid 132 can thus accumulate in the bladder 130.

When bladder drainage is desired, the patient palpates his penis at the penile meatus to locate the palpation lobes 68 and 70 on the cuff 60. Location of the palpation lobes 68 and 70 leads to location of the palpation flats 69 and 71. The patient then palpates the penis at the palpation flats 69 and 71 exerting slight pressure thereon to cause the duckbill valve portions 50 and 52 to deflect into an open position in the manner shown in FIGS. 6 and 10.

The valve means 48 is thus palpated into an open condition enabling the bladder fluid 132 to flow through the drainage passage 20, past the duckbill valve portions 50 and 52, and out of the urethra 128.

When a bladder drainage is completed, the palpation pressure of the fingers on the palpation flats 69 and 71 is released. Removal of palpation pressure from the palpation flats 69 and 71 enables the duckbill valve portions 50 and 52 to resume their normally closed position, thereby shutting off the fluid drainage passage 20 and allowing the bladder fluid 132 to accumulate in the bladder 130.

A patient can thus control and limit bladder discharge as he chooses. As will be apparent, the incontinence portion 12 which permits such control is entirely recessed in the penis and substantially undetectable.

If there is a need to remove the incontinence portion 12 from the urethra 128, the penis is collapsed against the pubis, exposing the valve junction 46. The tube member 16 is cut just proximal to the valve junction 46 to enable the bladder balloon 30 and the urethral cuff 32 to deflate. The incontinence portion 12 can then be removed.

Another embodiment of the catheter assembly is generally indicated by the reference number 140 in FIG. 11. The catheter assembly 140 includes an incontinence portion 142 comprising a tubular member 144 which can be formed of silicone. The tubular member 144 includes a spiral-shaped bladder engaging portion 146 at one end thereof and a valve junction 148 at an opposite end thereof. A flexible, extendable resilient noninflatable urethral cuff 150 which can be formed of silicone is provided on the tubular member 144 between the spiral bladder engaging portion 146 and the valve junction 148.

The spiral bladder engaging portion 146 defines a spiral passage 153 and is provided with a plurality of openings 152 that communicate with the spiral passage 153. The spiral passage 153 communicates with a fluid drainage passage 154 formed in the tubular member 144. However, the spiral bladder engaging portion 146 has a closed free end portion 156.

The valve junction 148 is similar to the valve junction 46 but does not include inflation lumen. The valve junction 148 includes a peripheral cuff portion 158 formed with oppositely disposed palpation lobes 160 and 162 and palpation flats 161 and 163 oriented in an arrangement similar to that of the valve junction 46. A valve means 165 having normally closed duckbill valve portions 164 and 166 close off the fluid drainage passage 154 in the tubular member 144. The valve junction 148 also includes a tubular extension 168 defining an extension passage 170.

The incontinence portion 142 of the catheter assembly 140 can be used in combination with a drainage member (not shown) that permits continuous bladder drainage. However, the incontinence portion 140 can also be used without a drainage member, as an incontinence device, for user controlled bladder drainage In using the catheter assembly 140 as an incontinence device, a stylet member 172 is inserted into the extension passage 170 through the fluid drainage passage 154 and into the spiral passage 153 (FIG. 13) to distend and straighten the spiral configuration of the bladder engaging portion 146 as shown in FIG. 12. The stylet 172 is also used to elongate the urethral cuff 150 to facilitate insertion of the incontinence portion 142 in a urethra 174 as shown in FIG. 12.

Once the distended spiral engaging portion 146 is disposed in a bladder 176, the stylet 172 is withdrawn enabling the distended portion 146 to reform as a spiral and engage the bladder 176. Withdrawal of the stylet 172 also enables the distended urethral cuff 150 to reform as shown in FIG. 13. The urethral cuff 150 helps maintain the stable positioning of the tubular member 144 in the urethra 174.

When a bladder discharge is desired, the user or patient palpates the cuff portion 158 to locate the palpation bulges 160 and 162 and the palpation flats 161 and 163. Slight depression of the palpation flats 161 and 163 causes the duckbill valve portions 164 and 166 to deflect into an open position permitting communication between the fluid drainage passage 154 and the extension passage 170. Bladder fluid can thus be discharged through the openings 152 in the spiral bladder engaging portion 146 through the spiral passage 153 and into the fluid drainage passage 154 for elimination through the extension passage 170.

When palpation of the palpation flats 161 and 163 ceases, the duckbill valve portions 164 and 166 return to the normally closed position shutting off the flow of fluid past the duckbill valve portions 164 and 166. A secure, leak-tight seal of fluid is provided by the valve means 165 when the duckbill valve portions 164 and 166 are in their normally closed position.

The catheter assembly 140 can be installed as a continuous drainage catheter by combining a drainage member (not shown) with the incontinence portion 142 before urethral insertion. Although not shown, the drainage member for the catheter assembly 140 is a modified drainage/ inflation member 14 without inflation needles 96, 98, without syringe receivers 114 and 116 and without inflation lumen 86, 88. However, the modified drainage member (not shown) is otherwise similar to the member 14 and includes a duct extension 106 (FIG. 1) with a free end portion 108 extending from a drainage duct 78. An opposite end of the drainage duct 78 is provided with a drainage extension 112 without syringe receivers 114 and 116.

Since the modified drainage member is not shown, reference is made to the drainage member 14 upon which the modified drainage member is based. The modified drainage member is joined with the incontinence portion 142 such that the duct extension 106 engages the duckbill valve portions 164 and 166 to maintain such valve means 165 in an open condition. A stylet (not shown), similar to the stylet 72 but more elongated, is inserted through the modified drainage member and into the tubular member 144 before the incontinence portion 142 is inserted in the urethra 174. Urethral insertion is then accomplished in a manner similar to that previously described for the catheter assembly 10.

Conversion of the catheter assembly 140 from the continuous drainage arrangement just described to user-controlled bladder drainage is accomplished by detaching the modified drainage member (not shown) from the tubular extension 168 while the incontinence portion 142 remains in the urethra 174.

Removal of the incontinence portion 142 from the urethra 174 is preceded by insertion of the stylet 172 in the extension passage 170. The stylet 172 is inserted past the duckbill valve portions 164 and 166 and into the fluid drainage passage 154 for reception in the spiral passage 153 to straighten the spiral engaging portion 146 and distend the urethral cuff 150 as shown in FIG. 12. The removal operation is facilitated by collapsing the penis against the pubis to expose the valve junction 148. The valve junction 148 can thus be gripped while the stylet 172 is used to straighten the spiral bladder engaging portion 146 and distend the urethral cuff 150.

Another embodiment of the catheter assembly is generally indicated by the reference number 180 in FIG. 14. The catheter assembly 180 includes an incontinence portion 182 comprising a tubular member 184 which can be formed of silicone, hytrel or any other suitable known biocompatible thermoplastic. The tubular member 184 includes a Malecot bladder engaging portion 186 at one end thereof and a valve junction 188 at an opposite end thereof.

The Malecot bladder engaging portion 186 which can be formed of hytrel or any other suitable known biocompatible thermoplastic includes four resilient distendible bowed strips 190, 192, 194 and 196 that join the tubular member 184 at tubular sections 198 and 200. A fluid drainage passage 202 extends through the tubular member 184, including the tubular sections 198 and 200. However the tubular section 200 is formed with a closed free end 204.

A urethral cuff 206 identical to the urethral cuff 150 is formed on the tubular member 184. The valve junction 188 is identical to the valve junction 148 of the catheter assembly 140.

The valve junction 188 thus includes a cuff portion 158 with opposite palpation lobes 160, 162 and opposite palpation flats 161 and 163. The valve junction 188 also includes the valve means 165 with normally closed duckbill valve portions 164 and 166 that close off the fluid drainage passage 202.

The incontinence portion 182 of the catheter assembly 180 can be used in combination with a drainage member (not shown) of the type previously described for use in the catheter assembly 140. However the incontinence portion 182 can also be used without a drainage member, as an incontinence device, for user controlled bladder drainage.

The catheter assembly 180, when used as an incontinence device, is installed in the urethra and bladder using the stylet member 208.

Referring to FIGS. 15 and 16, the stylet member 208 is inserted into the extension passage 170 of the valve junction 188 in the direction of the arrow 210. The stylet 208 is forced against the closed end 204 of the tubular section 200 to exert a distention force that straightens and distends the bowed strips 190, 192, 194 and 196 of the Malecot bladder engaging portion 186 and straightens and distends the urethral cuff 206 as shown in FIG. 19. The distended incontinence portion 182 is thus inserted in the urethra 174 and the bladder 176.

Subsequent removal of the stylet 208 permits the Malecot strips 190, 192, 194 and 196 to reassume their bowed form and engage against the bladder 176. The urethral cuff 206 likewise reassumes the cuff-shape to bear against the urethra 174. User controlled bladder drainage is accomplished by palpating the valve means 165 through the penis in a manner similar to that previously described.

If the catheter assembly 180 is to be installed for continuous drainage of the bladder 176, then a drainage member similar to that previously described in connection with the catheter assembly 140 must first be joined to the incontinence portion 182 before the incontinence portion is inserted in the urethra 174. Once the incontinence portion 182 is inserted in the urethra 174, it is not feasible to connect the previously described drainage member (not shown) without first removing the incontinence portion 182 from the urethra 174.

However, if the catheter assembly 180 is installed for continuous drainage purposes with a drainage member, it can be adapted to function as a user controlled incontinence device without removing the incontinence portion 180 from the urethra 174. This limitation is also true of the catheter assembly 140.

Other palpatable valve arrangements can be used with the incontinence portions 12, 142 and 182 of the catheter assemblies 10, 140 and 180. For example, referring to FIG. 17, a valve junction 220 comprises a cuff portion 222 with opposite palpation lobes 224, 226 and opposite palpation flats (not shown) oriented in a manner similar to that previously described for the valve junction 148.

The valve junction 220 includes valve means 228 having a deflectable valve member 230 with a cross-shaped slit 232 that deflects to an open position upon palpation of the palpation flats (not shown). The valve member 230 and cross-shaped slit 232 are otherwise in a normally closed condition as shown in FIG. 17.

The arrow 234 in FIG. 17 indicates the direction of flow of bladder fluid in a fluid drainage passage 238 past the valve means 228 to an extension passage 240 which leads to the urethral opening (not shown). The valve means 228 is thus manually manipulable through the penis to an open condition for user controlled bladder drainage.

A valve junction with another palpatable valve arrangement is generally indicated by the reference number 250 in FIG. 18. The valve junction 250 includes valve means 252 having a deflectable valve member 254 formed with four corner slits of L-shape such as 256 and 258 that are normally in a closed condition. The valve member 254 normally urges a sealing ball 260 against a valve seat 262 having a valve opening 264. The valve junction 250 also includes a cuff portion 266 with opposite palpation lobes 268, 270 and opposite palpation flats (not shown) having an orientation similar to that of the valve junction 148.

Palpation of the valve means 252 in a manner similar to that previously described for the valve means 250, causes deflection of the valve seat 262 and deflection of the valve member 254 to unseat the sealing ball 260 and open the slits 256 and 258. The arrow 272 indicates the direction of bladder fluid drainage from a fluid drainage passage 274 to an extension passage 276 which leads to the urethral opening. The valve means 252 is thus manually manipulable through the penis to an open condition for user controlled bladder drainage.

Another embodiment of a catheter assembly is generally indicated by the reference number 280 in FIG. 19. The catheter assembly 280 comprises an incontinence portion 282 including a tubular member 284 which can be formed of silicone. The tubular member 284 is provided with a funnel-shaped bladder engaging portion 286 in proximity of a tubular end portion 288 having an opening 290. The funnel-shaped bladder engaging portion 286 is formed of a flexible resilient compressible material such as silicone.

Valve means 292 are provided at an opposite end portion 293 of the tubular member 284. The valve means 292 is formed integrally with the tubular member 284 and includes a valve member 294 formed with a cross-shaped slit 296. An annular palpation lobe 298 is formed at the periphery of the valve member 294.

A funnel-shaped urethral engaging portion 302 of the same material as the bladder engaging portion 286 is formed on the tubular member 284 a predetermined distance from the bladder engaging portion 286.

The catheter assembly 280 can be used for continuous bladder drainage with a drainage member (not shown) of the type previously described for the catheter assembly 140, wherein the drainage member engages the normally closed valve means of the incontinence portion 282 in order to maintain the deflectable valve member 294 in an open condition.

The catheter assembly 280, when used for continuous bladder drainage purposes, is installed in the urethra with the drainage member (not shown) attached.

Whether the catheter assembly 280 is installed for continuous bladder drainage or user controlled bladder drainage (without a drainage member) an installation sleeve 304 is first engaged around the tubular member 284 to compress and enclose the funnel-shaped bladder engaging portion 286 and the funnel-shaped urethra engaging portion 302.

The sleeve 304, with the incontinence portion 282 disposed therein (FIG. 20) is inserted in the urethra. When a desired insertion position is attained, a push catheter 306 is inserted in the end of the sleeve 304 to block the incontinence portion 282 as the sleeve 304 is removed from the urethra.

Once the sleeve 304 is withdrawn, the funnel-shaped bladder engaging portion 286 and urethral engaging portion 302 expand to their normal shape to engage the bladder 300 and the urethra 301 thereby maintaining the tubular member 284 in a predetermined urethral position.

The valve means 292 is aligned with the penile meatus and the normally closed valve member 294 prevents bladder fluid from draining outwardly of the tubular member 284.

When bladder drainage is desired, the annular palpation lobe 298 is palpated through the penis to cause the valve member 294 to deflect. Deflection of the valve member 294 causes the cross slit 296 to open permitting bladder fluid that enters the tubular member 284 through the opening 290 to drain through the fluid drainage passage 308, past the cross slit 296 and out of the urethra.

To remove the incontinence portion 282 the penis is collapsed against the pubis exposing the valve means 292. The valve means 292 is gripped, for example, by pinching between the thumb and forefinger, and the sleeve member 304 is slid over the tubular member 284 to again collapse the funnel-shaped bladder engaging portion 286 and urethra engaging portion 302. The sleeve member 304 and encased incontinence portion 282 are then withdrawn from the urethra 301 and bladder 300.

Another embodiment of a catheter assembly is generally indicated by the reference number 320 in FIG. 22. The catheter assembly 320 includes an incontinence portion 322 joined to a drainage/inflation member 324. The incontinence portion 322 includes a tubular member 326 substantially similar to the tubular member 16 of the catheter assembly 10.

The incontinence portion 322 further includes a valve junction 328 comprising a tubular extension 329 that interconnects with an end portion 330 of the tubular member 326.

The valve junction 328 includes lumen portions 332 and 334 that are noncommunicable with a valve junction fluid passage 336. The lumens 332 and 334 have respective diverging valve seats 338 and 340 that form respective continuations of inflation lumens 342 and 344 in the tubular member 326. Valve balls 346 and 348 are respectively provided in the diverging valve seats 338 and 340 of the lumens 332 and 334. Large diameter and small diameter annular inserts 350 and 352 reinforce the diverging valve seats 338 and 340.

Referring to FIGS. 22 and 25, a valve means 354 provided in the valve junction 328 includes a slidable valve member 356 constrained to slide transversely of the tubular extension 329 in a transverse opening 331 (FIG. 25). The valve member 356, which can be formed of stainless steel or a rigid biocompatible plastic such as polycarbonate or polysulfone, includes a stem 360 with enlarged capsule-shaped end portions 362 and 364. The capsule-shaped end portion 364 is of greater transverse extent than the capsule-shaped end portion 362.

The capsule-shaped end portions 362 and 364 have a predetermined fit in the transverse opening 331 such that the valve member 356 will slidably move in the transverse opening 331, yet remain detented wherever it has been moved because of such predetermined fit.

A flexible, stretchable tubular envelope 366 which can be formed of silicone encases the tubular extension 329 forming a leak-tight enclosure around the capsule-shaped end portions 362 and 364. The transverse extent of the valve means 354 exceeds the cross-sectional diameter of the tubular extension 329 and the tubular envelope 366 by a predetermined amount. Consequently one of the capsule-shaped end portions 362 or 364 will always project transversely beyond the tubular extension 329 by a predetermined amount that exceeds the thickness of the tubular envelope 366. The projection of the capsule-shaped end portions 362 and 364 thus constitutes the palpation means for palpating the valve member 356 to a desired position.

The incontinence portion 322 is otherwise similar to the incontinence portion 12 having an inflatable bladder balloon (not shown) and an inflatable urethral cuff (not shown) identical to the bladder balloon 30 and inflatable urethral cuff 32.

The drainage/inflation member 324 includes an adapter portion 370 having an end 372. A pair of inflation needles 374 and 376 which communicate with inflation lumens 378 and 380 of the drainage/inflation member 324 project from the end 372. A pair of recesses 382 and 384 are formed in the end 372 around the needles 374 and 376 for leak tight reception of the lumens 332 and 334 of the valve junction 328 as shown in FIG. 23. A duct passage 386 formed within the drainage/inflation member 324 extends to a neck 388 at the end 372. The remaining structure of the drainage/inflation member 324 is otherwise similar to the drainage/inflation member 14.

In using the catheter assembly 320, the drainage/inflation member 324 is joined to the incontinence portion 322 by aligning the inflation needles 374 and 376 with the lumen portions 332 and 334 of the valve junction 328 and engaging such needles in the respective lumen portions 332 and 334. During such engagement the needles 374 and 376 urge the valve balls 346 and 348 away from their respective diverging valve seats 338 and 340. The neck 388 is simultaneously received in the fluid passage 336 of the valve junction 328 to permit communication between the duct passage 386 and the fluid passage 336.

With the catheter assembly 320 engaged as shown in FIG. 23, the incontinence portion 322 is inserted in the urethra and bladder (not shown). During such insertion the adapter end portion 370 is also received in the urethra.

A bladder balloon (not shown) similar to the bladder balloon 30 and an inflatable urethral cuff (not shown) similar to the urethral cuff 32, are inflated through the drainage/inflation member 324 in the manner previously described for the catheter assembly 10. Fluid pressure within the lumens 378, 332 and 342 as well as 380, 334 and 344 maintain the inflated condition of the inflatable bladder balloon and the inflatable urethral cuff.

When the slidable valve member 356 is palpated through the penis (not shown) at the capsule end 364, the valve member 356 is moved into a closed condition in the valve junction fluid passage 336 thereby closing off the fluid passage 336, as shown in FIGS. 26 and 28. The valve member 356 thus prevents bladder fluid from passing into the drainage/inflation member 324. In order to place the slidable valve member 356 in an open condition, the capsule end 362 is palpated as shown in FIGS. 25 and 27 to position the stem portion 360 in the valve junction fluid passage 336.

Since the valve member 356 will remain detented in its selected palpated position there will be continuous bladder drainage when the valve member is palpated to the open position of FIGS. 25 and 27.

If a patient is capable of palpating the valve member 356 to the open or closed condition, the drainage/inflation member 324 can be removed after the bladder balloon (not shown) and urethral cuff have been inflated.

Removal of the drainage/inflation member 324 is accomplished in the manner previously described for removal of the drainage/inflation member 14. Separation of the inflation needles 374 and 376 from the inflation lumen 332 and 334 causes the fluid pressure within the inflation lumen 342 and 344 to urge the valve sealing balls 346 and 348 into their respective diverging valve seats 338 and 340 to the positions shown in FIG. 22. The inflation lumens 342 and 344 are thus closed by the valve sealing balls 346 and 348 thereby preventing the bladder balloon and urethral cuff from deflating.

To remove the catheter assembly 320 from the urethra and bladder, the penis is collapsed against the pubis exposing the valve junction 328 which can be cut just beyond the valve sealing balls 346 and 348. Inflation fluid can flow outwardly of the lumen 342 and 344 enabling the bladder balloon and urethral cuff to deflate. The incontinence portion 322 can then be removed.

As will be apparent to those skilled in the art, the valve junction portions of some of the embodiments can be interchanged.

Some advantages of the invention evident from the foregoing description include a urethral indwelling catheter with incontinence control that provides the option of continuous bladder drainage as well as the option of usercontrolled bladder drainage. Either option can be obtained with just one installation of a catheter assembly in the urethra and bladder.

A further advantage is that the valve means for controlling movement of fluid from the bladder are palpatable in a predetermined direction to an open condition and include palpation means having predetermined surface characteristics to permit manual sensing of the predetermined palpation direction for palpating the valve means to the open condition.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An indwelling urethral catheter comprising
 (a) a flexible elongated tubular member having a fluid drainage passage,
 (b) engaging means at one end portion of said tubular member for engaging the wall portion of a bladder, said tubular member having an opening at said one end portion for communication with said fluid drainage passage for drainage of fluid from said bladder into said fluid drainage passage,
 (c) valve means at an opposite end portion of said tubular member for controlling movement of fluid through said drainage passage from said bladder, said valve means having a closed condition, and being palpatable in a predetermined palpation direction to an open condition, and
 (d) palpation means for said valve means having a predetermined surface characteristic to permit manual sensing of the predetermined palpation direction for palpating said valve means to said open condition.

2. The catheter as claimed in claim 1 wherein said valve means include a deflectable valve portion that is deflectable to said open condition upon palpation of said palpation means in said predetermined palpation direction.

3. The catheter as claimed in claim 2 wherein said valve means has a periphery and said predetermined surface characteristics comprise at least two oppositely disposed palpation lobes formed at first opposite portions of said periphery.

4. The catheter as claimed in claim 3 wherein said predetermined surface characteristics comprise at least two palpation flats formed at second opposite portions of said periphery offset a predetermined amount from said first opposite portions, said deflectable valve portion being flexible and flexing to form an opening when a predetermined palpation pressure is applied to said palpation flats.

5. The catheter as claimed in claim 4 wherein said flexible deflectable valve portion is a duckbill valve and flexes to form an opening when said palpation pressure is applied to said palpation flats to place said valve means in said open condition.

6. The catheter as claimed in claim 4 wherein said valve means includes a valve sealing ball and a valve seat, said deflectable valve portion normally biasing said valve sealing ball against said valve seat to maintain said valve means in a normally closed condition, said deflectable valve portion including at least one normally closed slit and being deflectable to form an opening at said slit and relieve the bias on said valve sealing ball to unseat said ball from said valve seat when said palpation pressure is applied to the palpation flats of said valve periphery to place said valve means in said open condition.

7. The catheter as claimed in claim 4 wherein said deflectable valve portion includes at least one normally closed slit and is deflectable to form an opening at said slit to place said valve means in said open condition when said palpation pressure is applied to said palpation flats at said second opposite portions of said valve periphery.

8. The catheter as claimed in claim 2 wherein said deflectable valve portion comprises a slidable valve member having open and closed positions, said valve member having opposite valve ends, one of said valve ends projecting from said tubular member to constitute said predetermined surface characteristic when said valve member is in one of said open and closed positions, said slidable valve member being moveable in said predetermined palpation direction to the other of said open and closed positions when a predetermined palpation pressure is applied at said one valve end.

9. The catheter as claimed in claim 8 wherein said valve member includes a reduced section that aligns with said fluid drainage passage when said valve member is moved to said open position.

10. The catheter as claimed in claim 8 wherein said valve member includes an enlarged section that aligns with said fluid drainage passage to close said fluid drainage passage when said valve member is moved to said closed position.

11. The catheter as claimed in claim 1 wherein said engaging means includes an inflatable portion, said catheter further including inflation means for inflating said inflatable portion.

12. The catheter as claimed in claim 1 wherein said engaging means includes a flexible spiral portion.

13. The catheter as claimed in claim 12 further including a stylet for insertion in said fluid drainage passage to straighten said spiral portion to facilitate positioning of said catheter in said urethra.

14. The catheter as claimed in claim 1 wherein said engaging means includes a flexible Malecot portion.

15. The catheter as claimed in claim 14 further including a stylet for insertion in said fluid drainage passage to straighten and distend said Malecot portion to facilitate positioning of said catheter in said urethra.

16. The catheter as claimed in claim 1 wherein said engaging means include a flexible funnel-shaped portion.

17. The catheter as claimed in claim 16 further including a sleeve for surrounding said tubular portion to compress said funnel-shaped portion within the confines of said sleeve to facilitate positioning of said catheter in said urethra and bladder.

18. The catheter as claimed in claim 1 further including means for draining fluid detachably joined to the opposite end portion of said tubular member to communicate with said fluid drainage passage, said means for draining fluid including a duct member having an outlet opening and a valve engaging portion for actuating said valve means into said open condition to permit unobstructed drainage of fluid from said fluid drainage passage through said valve means to said outlet opening.

19. An indwelling urethral catheter comprising
(a) a flexible elongated tubular member having a fluid drainage passage,
(b) first and second engaging means spaced on said tubular member for respectively engaging the wall portion of a bladder and said urethra to stabilize the position of said catheter in said urethra and bladder, said tubular member having an opening in proximity of said first engaging means for communication with said fluid drainage passage for drainage of fluid from said bladder into said fluid drainage passage,
(c) valve means at an opposite end portion of said tubular member for controlling movement of fluid through said drainage passage from said bladder, said valve means having a closed condition, and having an open condition,
(d) said valve means having a deflectable valve member that is deflectable upon palpation of said valve means in a predetermined palpation direction to place said valve means from said closed condition to said open condition, and at least one palpation surface at said valve means having a predetermined surface characteristic to permit manual sensing of the predetermined palpation direction to facilitate palpation of said deflectable valve member to said open condition.

20. The catheter as claimed in claim 19 wherein said deflectable valve member includes a slide member having said one palpation surface with said predetermined surface characteristic, said slide member being slidably moveable to said open condition upon palpation of said one palpation surface, said slide member including a reduced section that aligns with said fluid drainage passage when said slide member is moved to said open condition.

21. The catheter as claimed in claim 20 further including a second palpation surface on said slide member, said second palpation surface having said predetermined surface characteristic, said slide member including an enlarged section, said slide member being moveable to said closed condition upon palpation of said second palpation surface to move said enlarged section into alignment with said fluid drainage passage to block said fluid drainage passage.

22. The catheter as claimed in claim 19 wherein said deflectable valve member is flexible and compressible and includes two of said palpation surfaces with said predetermined surface characteristic, such that palpation of said valve means at said two palpation surfaces causes said valve means to be placed in said open condition.

* * * * *